United States Patent [19]
Boller et al.

[11] 3,981,817
[45] Sept. 21, 1976

[54] MIXTURES OF LIQUID CRYSTALS

[75] Inventors: Arthur Boller, Binningen; Hanspeter Scherrer, Therwil, both of Switzerland

[73] Assignee: Hoffmann-La Roche Inc., Nutley, N.J.

[22] Filed: Mar. 27, 1974

[21] Appl. No.: 455,083

[30] Foreign Application Priority Data
Apr. 4, 1973 Switzerland.......................... 4799/73

[52] U.S. Cl................................ 252/299; 350/150; 350/160 LC
[51] Int. Cl.²............................................ G02F 1/16
[58] Field of Search...................... 252/408 LC, 299

[56] References Cited
UNITED STATES PATENTS
| | | | |
|---|---|---|---|
| 3,795,436 | 3/1974 | Boller | 350/150 |
| 3,796,479 | 3/1974 | Helfrich | 350/150 |

FOREIGN PATENTS OR APPLICATIONS
| | | | |
|---|---|---|---|
| 2,234,522 | 1/1973 | Germany | 252/299 |
| 2,306,739 | 8/1973 | Germany | 252/299 |
| 2,024,269 | 12/1971 | Germany | 252/299 |

OTHER PUBLICATIONS
Article of Boller et al. "Proceedings of IEEE," Aug. 1972, pp. 1002–1003.
Usoltseva et al., Chemical Characteristics, Structure & Properties of Liquid Crystals, 9/63.

*Primary Examiner*—Samuel W. Engle
*Assistant Examiner*—Ralph Palo
*Attorney, Agent, or Firm*—Samuel L. Welt; Bernard S. Leon; William G. Isgro

[57] ABSTRACT

Liquid crystalline mixtures comprising at least three compounds of the formula

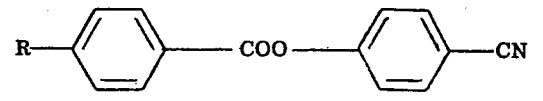

I wherein R is n-butyl, n-pentyl, n-hexyl, n-heptyl or n-octyl, which may additionally contain other nematic or non-nematic substances, are described. The liquid crystalline mixtures are useful, for example, as dielectrics for electro-optical purposes.

11 Claims, No Drawings

MIXTURES OF LIQUID CRYSTALS

BRIEF SUMMARY OF THE INVENTION

The invention relates to liquid crystalline mixtures comprising at least three compounds of the formula

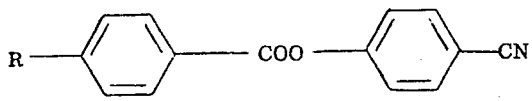

I wherein R is n-butyl, n-pentyl, n-hexyl, n-heptyl or n-octyl.

DETAILED DESCRIPTION OF THE INVENTION

The liquid crystalline mixtures of the invention contain at least three compounds of the formula

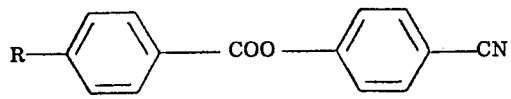

I wherein R is n-butyl, n-pentyl, n-hexyl, n-heptyl or n-octyl.

The compounds of formula I have, in the liquid crystalline state, a positive anisotropy of the dielectric constants ($\epsilon_\| > \epsilon_\perp$, $\epsilon_\|$ is the dielectric constant along the longitudinal axis of the molecule and $\epsilon_\perp$ is the dielectric constant perpendicular thereto).

In an electric field, the nematic liquid crystals in the mixtures of the present invention orientate themselves (because $\epsilon_\| > \epsilon_\perp$) with the direction of their largest dielectric constant, that is, with their longitudinal axes, parallel to the field direction. This effect is used, inter alia, in the interaction between embedded molecules and liquid crystalline molecules (guest-host interaction) described by J. H. Heilmeier and L. A. Zanoni [Applied Physics Letters 13, 91 (1968)]. A further interesting application of the dielectric field orientation is present in the rotation cell discovered by M. Schadt and W. Helfrich [Applied Physics Letters 18, 127 (1971)], as well as in the Kerr cell described in Molecular Crystals and Liquid Crystals 17, 355 (1972).

The electro-optical rotation cell of Schadt et al., supra, comprises essentially a condenser having transparent electrodes whose dielectric is formed by a nematic substance or liquid crystal having a dielectric constant of $\epsilon_\| > \epsilon_\perp$. The longitudinal axes of the molecules of the liquid crystal are arranged in twisted form between the condenser plates in the fieldless state. The twisting structure is defined by the given wall orientation of the molecules. After the application of an electrical potential to the condenser plates, the molecules adjust themselves with their longitudinal axes in the field direction, i.e., perpendicular to the surface of the plates, whereby linear polarized light is no longer rotated in the dielectric, that is, the liquid crystal is uniaxially perpendicular to the surface of the plates. This effect is reversible and can be used for electrically controlling the optical transmissivity of the condenser.

In such "light rotation cells", it is desirable to utilize liquid crystalline substances which have a low melting point, slight viscosity and good stability. The substances previously used for this purpose have the disadvantage of first showing nematic properties at relatively high temperatures so that electro-optical apparatuses provided with such liquid crystalline substances have to be heated and possibly thermostatted. Furthermore, the known liquid crystalline substances or liquid crystals possess a high viscosity which, for example, in an electro-optical apparatus, leads to considerable disadvantages because the operation thereof requires relatively large voltages and long response times.

It has now surprisingly been found that the mixtures provided by the present invention have not only the required large positive anisotropy of the dielectric constants and slight viscosity, but are liquid crystalline at relatively low temperatures. A further advantage of the mixtures provided by the present invention with respect to the substances previously used for this purpose is their much greater stability which enables these mixtures to be handled in a much easier manner. Their use in electro-optical apparatus is therefore possible using a lower voltage, shorter response time and without heating at room temperature.

The composition of the mixtures provided by the present invention is preferably selected to be one which corresponds to a eutectic. Mixtures which contain p-n-butylbenzoic acid p'-cyanophenyl ester, p-n-hexylbenzoic acid p'-cyanophenyl ester and p-n-octylbenzoic acid p'-cyanophenyl ester, are especially preferred.

The mixtures provided by the present invention can contain, in addition to at least three compounds of formula I, other nematic or non-nematic substances such as, for example, Schiff's bases of the formula

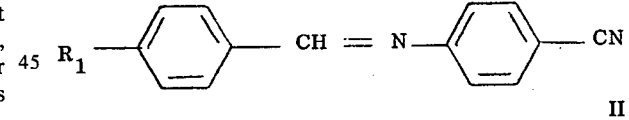

II wherein $R_1$ is straight-chain alkyl of 2 to 8 carbon atoms, straight-chain alkoxy of 4 to 7 carbon atoms or straight-chain alkanoyloxy of 2 to 8 carbon atoms.

Further, the mixtures provided by the present invention can also contain, in addition to at least three compounds of formula I, one or more compounds of the formula

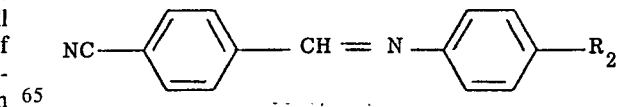

III wherein $R_2$ is straight-chain alkyl of 4 to 7 carbon atoms, or one or more compounds of the formula

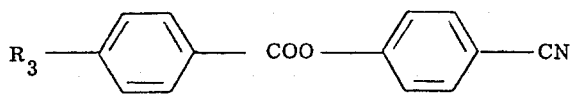

IV wherein $R_3$ is straight-chain alkoxy of 5 to 8 carbon atoms.

The mixtures provided by the present invention are prepared in accordance with the invention by warming the components to above their clearing point followed by thorough mixing.

Examples of the mixtures of the invention are compiled in Tables I and II. In Table III, the melting and clearing points of the individual compounds of the formula I are tabulated. As used herein in Tables I–III, $C_4$ denotes p-n-butylbenzoic acid p'-cyanophenyl ester, $C_5$ denotes p-n-pentylbenzoic acid p'-cyanophenyl ester, $C_6$ denotes p-n-hexylbenzoic acid p'-cyanophenyl ester, $C_7$ denotes p-n-heptylbenzoic acid p'-cyanophenyl ester and $C_8$ denotes p-n-octyl-benzoic acid p'-cyanophenyl ester.

TABLE III

| Compound | Melting Point in °C. | Clearing Point in °C. |
|---|---|---|
| $C_4$ | 67° | (41.5°)* |
| $C_5$ | 60.5° | (56°)* |
| $C_6$ | 44.5° | 47.5° |
| $C_7$ | 44° | 56.5° |
| $C_8$ | 46.5° | 54° |

*monotrope

The compounds of formula I can be prepared as follows:

A compound of the formula

V wherein R is as previously described, and Z is a leaving group, preferably a halogen, such as chlorine, is esterified with p-hydroxybenzonitrile. The esterification is conveniently carried out in an inert organic solvent, for example, an ether such as diethyl ether or tetrahydrofuran, dimethylformamide, benzene, toluene, cyclohexane or carbon tetrachloride. In order to bind the hydrogen halide liberated in the reaction, an acid binding agent is conveniently utilized. Suitable acid binding agents are tertiary amines such as pyridines, and the like. The acid binding agent conveniently is utilized in a large excess, so that it can simultaneously serve as a solvent as well as an acid binding agent. The temperature and pressure at which the esterification is carried out are not critical and, in general, atmospheric pressure and temperatures in the range of from about room

TABLE I

| Example | Mixture | Mixture ratio in mole/mole | Melting point in °C. | Clearing point in °C. |
|---|---|---|---|---|
| 1 | $C_8,C_6,C_4$ | 1:1:1 | 6.5° | 46.5° |
| 2 | " | 4:2:1 | 21° | 49° |
| 3 | " | 2:1:1 | 15° | 45.5° |
| 4 | " | 2:3:3 | 6.5° | 46° |
| 5 | " | 2:4:1 | 21.5° | 47.5° |
| 6 | " | 1:2:1 | 18° | 47.5° |
| 7 | " | 3:2:3 | 6.5° | 47° |
| 8 | " | 1:1:2 | 7.5° | 45° |
| 9 | " | 3:3:2 | 8° | 48° |
| 10 | $C_6,C_5,C_4$ | 1:1:1 | 31.5° | 48° |

TABLE II

| Example | Mixture | Mixture ratio in mole/mole | Melting point in °C. | Clearing point in °C. |
|---|---|---|---|---|
| 11 | $C_7,C_5,C_4$ | 1:1:1 | 26.5° | 51° |
| 12 | $C_8,C_5,C_4$ | 1:1:1 | 27° | 49° |
| 13 | $C_7,C_6,C_4$ | 1:1:1 | 7.5° | 48° |
| 14 | " | 4:2:1 | 25° | 52° |
| 15 | " | 2:4:1 | 33° | 49° |
| 16 | $C_8,C_7,C_4$ | 1:1:1 | 13° | 49.5° |
| 17 | " | 4:2:1 | 27° | 52° |
| 18 | " | 2:4:1 | 21.5° | 53° |
| 19 | $C_7C_6,C_5$ | 1:1:1 | 27° | 53° |
| 20 | $C_8C_6C_5$ | 1:1:1 | 16.5° | 51° |
| 21 | $C_8,C_7,C_5$ | 1:1:1 | 10.5° | 54° |
| 22 | " ":163; " | 4:2:1 | 28° | 53.5° |
| 23 | " | 2:4:1 | 25.5° | 54.5° |
| 24 | $C_8,C_7,C_6$ | 1:1:1 | 20.5° | 51.5° |
| 25 | $C_4,C_6,C_7,C_8$ | 1:1:1:1 | 6° | 48.5° |
| 26 | $C_5,C_6,C_7,C_8$ | 1:1:1:1 | 14° | 50° | temperature to about the boiling temperature of the reaction mixture are utilized.

The compounds of formula II and III are known compounds can be prepared according to procedures known in the art.

Preferred compounds of formula II are those wherein $R_1$ is straight-chain alkyl of 2 to 8 carbon atoms.

The compounds of formula IV can be prepared in analogy to the compounds of formula I. Preferred compounds of formula IV are p-n-hexyloxybenzoic acid p'-cyanophenylester and p-n-heptyl-oxybenzoic acid p'-cyanophenylester.

In the mixtures of the invention, the ratio of one compound to another should preferably not exceed 10. Essentially equimolar ratios are preferred.

We claim:

1. A mixture which contains p-n-octylbenzoic acid p'-cyanophenyl ester, p-n-hexylbenzoic acid p'-cyanophenyl ester and p-n-butylbenzoic acid p'-cyanophenyl ester in a molar ratio of 1:1:1.

2. A mixture which contains p-n-octylbenzoic acid p'-cyanophenyl ester, p-n-hexylbenzoic acid p'-cyanophenyl ester and p-n-butylbenzoic acid p'-cyanophenyl ester in a molar ratio of 2:1:1.

3. A mixture which contains p-n-octylbenzoic acid p'-cyanophenyl ester, p-n-hexylbenzoic acid p'-cyanophenyl ester and p-n-butylbenzoic acid p'-cyanophenyl ester in a molar ratio of 2:3:3.

4. A mixture which contains p-n-octylbenzoic acid p'-cyanophenyl ester, p-n-hexylbenzoic acid p'-cyanophenyl ester and p-n-butylbenzoic acid p'-cyanophenyl ester in a molar ratio of 3:2:3.

5. A mixture which contains p-n-octylbenzoic acid p'-cyanophenyl ester, p-n-hexylbenzoic acid p'-cyanophenyl ester and p-n-butylbenzoic acid p'-cyanophenyl ester in a molar ratio of 3:3:2.

6. A mixture which contains p-n-heptylbenzoic acid p'-cyanophenyl ester, p-n-hexylbenzoic acid p'-cyanophenyl ester and p-n-butylbenzoic acid p'-cyanophenyl ester in a molar ratio of 1:1:1.

7. A mixture which contains p-n-octylbenzoic acid p'-cyanophenyl ester, p-n-heptylbenzoic acid p'-cyanophenyl ester and p-n-butylbenzoic acid p'-cyanophenyl ester in a molar ratio of 1:1:1.

8. A mixture which contains p-n-octylbenzoic acid p'-cyanophenyl ester, p-n-hexylbenzoic acid p'-cyanophenyl ester and p-n-pentylbenzoic acid p'-cyanophenyl ester in a molar ratio of 1:1:1.

9. A mixture which contains p-n-octylbenzoic acid p'-cyanophenyl ester, p-n-heptylbenzoic acid p'-cyanophenyl ester and p-n-pentylbenzoic acid p'-cyanophenyl ester in a molar ratio of 1:1:1.

10. A mixture which contains p-n-butylbenzoic acid p'-cyanophenyl ester, p-n-hexylbenzoic acid p'-cyanophenyl ester, p-n-heptylbenzoic acid p'-cyanophenyl ester and p-n-octylbenzoic acid p'-cyanophenyl ester in a molar ratio of 1:1:1:1.

11. A mixture which contains p-n-pentylbenzoic acid p'-cyanophenyl ester, p-n-hexylbenzoic acid p'-cyanophenyl ester, p-n-heptylbenzoic acid p'-cyanophenyl ester and p-n-octylbenzoic acid p'-cyanophenyl ester in a molar ratio of 1:1:1:1.

* * * * *